United States Patent [19]

Prager et al.

[11] Patent Number: 5,698,142

[45] Date of Patent: Dec. 16, 1997

[54] PROCESS FOR THE PRODUCTION OF FINELY GRANULATED SOLID CHEMICAL COMPOUNDS

[75] Inventors: Avi Prager, Omer; Moti Veinberg, Meitar; Baruch Grinbaum, Tivon; Yehuda Keren, Kiryat Motzkin; Rafael Shemer, Kiryat Haim; Iulio Bitherfeld, Nahara; Leonid Zaslavsky, Haifa, all of Israel

[73] Assignee: Bromine Compounds, Ltd., Beer-Sheva, Israel

[21] Appl. No.: 640,066

[22] Filed: Apr. 30, 1996

[30] Foreign Application Priority Data

May 1, 1995 [IL] Israel ........................ 113562

[51] Int. Cl.$^6$ ........................ B29B 9/10
[52] U.S. Cl. ........................ 264/9; 264/140; 366/303; 366/307; 425/6; 425/209
[58] Field of Search ........................ 264/9, 140; 425/6, 425/209; 366/303, 307

[56] References Cited

U.S. PATENT DOCUMENTS

| | | | |
|---|---|---|---|
| 4,669,966 | 6/1987 | v. Deuren | 425/209 |
| 4,826,324 | 5/1989 | Kunz et al. | 366/307 |
| 4,889,431 | 12/1989 | Liechti | 366/303 |
| 5,121,992 | 6/1992 | List et al. | |
| 5,147,135 | 9/1992 | List et al. | 366/303 |
| 5,415,884 | 5/1995 | Manser et al. | 425/209 |

FOREIGN PATENT DOCUMENTS

| | | |
|---|---|---|
| 0 278 246 | 1/1987 | European Pat. Off. . |
| 0 619 137 | 10/1994 | European Pat. Off. . |

OTHER PUBLICATIONS

Patent Abstracts of Japan, vol. 5, No. 62 (C–052), Apr. 25, 1981 & JP-A-56 012328 (Ube Ind. Ltd.), Feb. 6, 1981, & Database WPI Derwent Publications Ltd., London GB; AN 81-22480.

Patent Abstracts of Japan, vol. 6, No. 41 (C–211), Feb. 22, 1984 & JP-A-58 199034 (Sumitomo Kinzoku Kogyo KK), Nov. 19, 1983.

*Primary Examiner*—Mary Lynn Theisen
*Attorney, Agent, or Firm*—Merchant, Gould, Smith, Edell, Welter & Schmidt, P.A.

[57] ABSTRACT

A method for the production of finely particulate solid chemical products from a molten stock comprises the steps of: (a) feeding the product, as molten stock, to an elongated treatment space, sealed from the ambient; (b) causing the product to flow as a flowable mass within space, while leaving a free portion of said space above the surface of said mass; (c) maintaining in said space an atmosphere that is non-reactive with said product; (d) subjecting said product to a stirring and mixing action by rotary means; (e) concurrently cooling said product as it proceeds along said space, whereby to solidify it; (f) concurrently detaching any product that adheres to surfaces within said space; and (g) discharging the solidified product, in the form of solid particles, from said elongated treatment space.

16 Claims, 2 Drawing Sheets

PROCESS FOR THE PRODUCTION OF FINELY GRANULATED SOLID CHEMICAL COMPOUNDS

FIELD OF THE INVENTION

The invention refers to the production of finely granulated solid chemical compounds, in particular, organic compounds requiring high purity, such as may be obtained, e.g., from a distillation process. It particularly refers to the production of particulate 4,4'-dihydrobiphenyl (hereinafter DHBP). It also refers to the use of specific fluid-mixing, heat transfer machinery for the aforesaid purpose.

BACKGROUND OF THE INVENTION

Various processes and apparatus are known for producing finely subdivided solid particles from molten chemical products. Examples of apparatus currently used in industry for this purpose are flakers and pastillators. Such apparatus, however, is not fully satisfactory for products solidified at relatively high temperatures, and the crystalline structure of the particles obtained is not fully satisfactory. Further, prior art apparatus cannot operate completely anaerobically and inevitably produces black oxidation products.

A particular example of a compound the production of which, in finely granulated solid form, has presented problems in the prior art, is the aforementioned DHBP, although the invention is not restricted to the treatment of said chemical compound. DHBP is produced by distillation, as will be hereinafter explained, in liquid form and must thereafter be solidified to finely subdivided particles. However, heretofore it has been found very difficult to control the size distribution of the particles and particularly, to avoid the formation of particles having linear dimensions below 0.1 mm and to obtain a product having high flowability, free from oxidized products, appearing as black specs, and at least 99.5% pure, as desired.

It should be understood that when reference is made to "particles", this term may include flakes, chips, granules, and any other particulate form.

The methods of the prior art have also not permitted to obtain DHBP in a highly crystalline state.

It is a purpose of this invention to overcome the drawbacks of the prior art and to provide a process for producing finely particulated solid chemical products in a highly pure state.

It is another purpose of this invention to provide such a process which yields a granulated product having high flowability.

It is a further purpose of this invention to provide such a process which yields a product with the desired granule size distribution and the desired crystalline structure.

It is a still further purpose of this invention to provide such a process particularly adapted to the production of particulate solid DHBP.

It is a still further purpose of this invention to provide such a process which is simple and economical to operate, and can be easily combined with existing production liens.

It is a still further purpose of this invention to provide means for carrying out the said process.

Other purposes and advantages of this invention will appear as the description proceeds.

SUMMARY OF THE INVENTION

The method according to the invention for the production of finely particulate solid chemical products from a molten stock of such products, particularly of DHBP, obtained e.g. from a production and purification line, which method comprises the steps of:

feeding the product, as molten stock, to an elongated treatment space, sealed from the ambient;

causing the product to flow as a flowable mass within space, while leaving a free portion of said space above the surface of said mass;

maintaining in said space an atmosphere that is non-reactive with said product, generally an oxygen-free or inert atmosphere;

subjecting said product to a stirring and mixing action by rotary means;

concurrently cooling said product as it proceeds along said space, whereby to solidify it;

concurrently detaching any product that adheres to surfaces within said space; and discharging the solidified product, in the form of solid particles, from said elongated treatment space.

The molten product is preferably cooled by heat exchange with cooled surfaces within as well as at the periphery of its fluid mass.

The elongated treatment space is preferably substantially cylindrical and, more preferably, horizontal; and the heat exchange within the fluid mass preferably begins along a cylindrical surface about the axis of the cylindrical space and irradicates radially outwards therefrom.

The ratio of the fluid mass of the product treated and the volume of the treatment space depends on the particular material being treated, but is preferably comprised between 50% and 75%, and more preferably, between 60% and 75%.

The product flowable mass is impelled to flow along the elongated treatment space by the pressure of the molten stock fed into said space at its inlet end.

The factors which determine the final particle size and its crystalline structure are the nature of the cooling medium (which may be e.g. water or preferably oil), its temperature, and the intensity of the stirring and mixing action to which the product is subjected, which is generally dependent of rotational speed of the rotary means employed.

The machinery which permits to carry out the process of the invention, though it is not intended, according to the art, for this purpose, is available on the market. An example is the mixing machine called REACTOTHERM RTC 16 of Krauss Maffei and DISCOTHERM B of List. Such a machine will be briefly described hereinafter.

Correspondingly, an aspect of the invention is the use, for producing solid particles from a molten stock of a chemical product, of an apparatus comprising:

a preferably cylindrical shell defining an elongated inner space sealed from the ambient;

means for filling said space within said shell with inert gas;

a plurality of rotary arms actuated for rotation by a shaft positioned substantially axially of said space;

a plurality of stationary arms positioned peripherally of said space for interaction with the rotary arms, to clean the same from adhered material, whereby to prevent its polimerization, decomposition or oxidation with the passage of time;

first cooling means, preferably located within said shaft and said rotary arms, for cooling any molten material located in said space;

second cooling means, located at the periphery of said shell inlet means for feeding a molten product stock to said space; and outlet means for discharging solidified product, in particular form, therefrom.

It is to be noted that all apparatus known in the art for producing granulated DHBP, or the like, is based on the principle of dividing the molten product stock into molten particles or drops and then separately sodifying said particles, or of producing a wholly solidified mass and then mechanically dividing it into particles, by grinding or milling or the like. In contrast to these principles, the present invention creates a flowable mass comprising solid and molten product, and gradually transforms it into completely solid product, which however is in the form of separate small particles, although no mechanical action has been applied to said mass to cause such a particulation. How this occurs, is not fully understood and is unexpected and surprising, and the applicant does not wish to be bound to any theoretical physical explanation of this phenomenon, but only to the experimental fact that it indeed occurs.

DETAILED DESCRIPTION OF PREFERRED EMBODIMENTS

Figure 1:
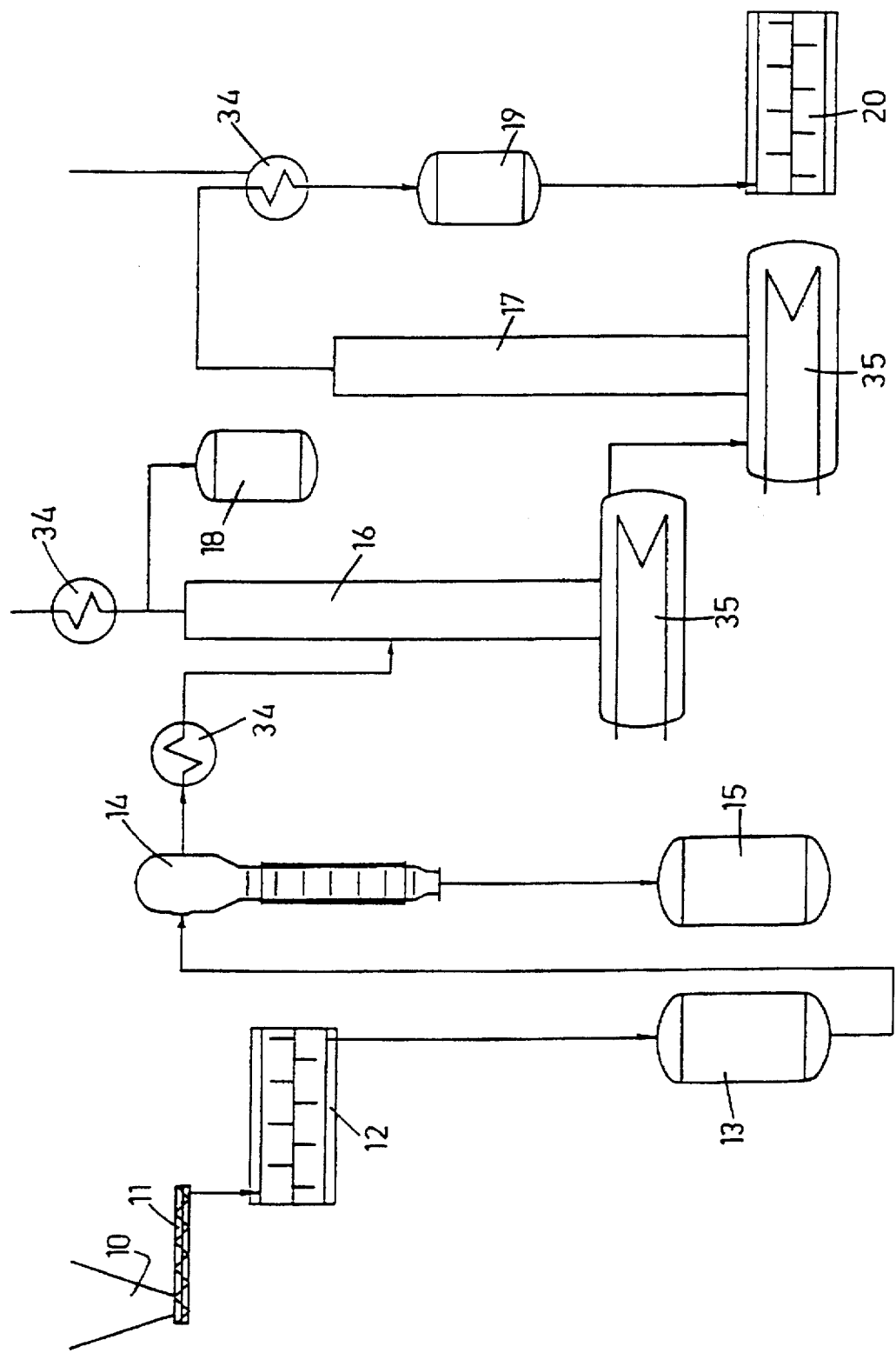
FIG. 1 is a schematic illustration of the flow diagram of a distillation system of a chemical product, particularly DHBP.

As has been said, the invention is particularly useful for the treatment of DHBP, but is not in any way limited thereto. The schematic flow diagram of the DHBP distillation system shown in FIG. 1 can be taken generally to describe a typical flow diagram of a purification system of a chemical product, from which high purity is required. The crude starting material, in conveniently comminuted form, is charged into a funnel 10 and passes to a solid feeder 11, from which it is fed into a melter 12. From the melter 12 it is discharged in liquid form to an intermediate storage vessel 13, from which it is fed to a first evaporation, generally indicated at 14. High boiling organic materials and inorganic materials (heavies) fall into a vessel 15 and are removed from the cycle. The purified lighter material is fed to a distillation system comprising two columns, 16 and 17, of any suitable conventional type. The light fractions distilled in first column 16 are discharged into vessel 18. Numeral 34 indicates condensers and numeral 35 indicates reboilers. The purified product, specifically DHBP, flows from the second column to a vessel 19 and from it to the apparatus 20 for the production of solid particles, e.g. the apparatus illustrated in FIGS. 2 and 3.

Figure 2:
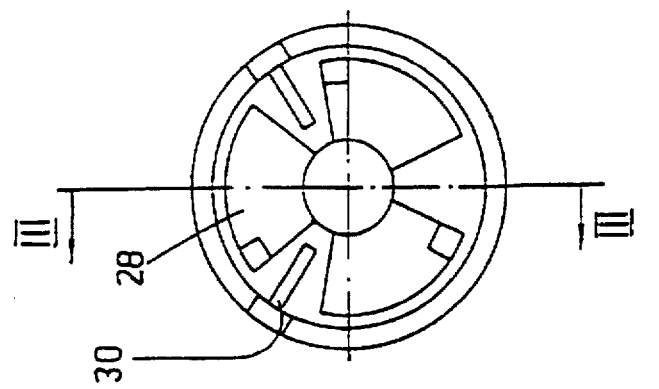
FIG. 2 is a schematic axial cross-section of a machine adapted for carrying the invention into practice.
Figure 3:
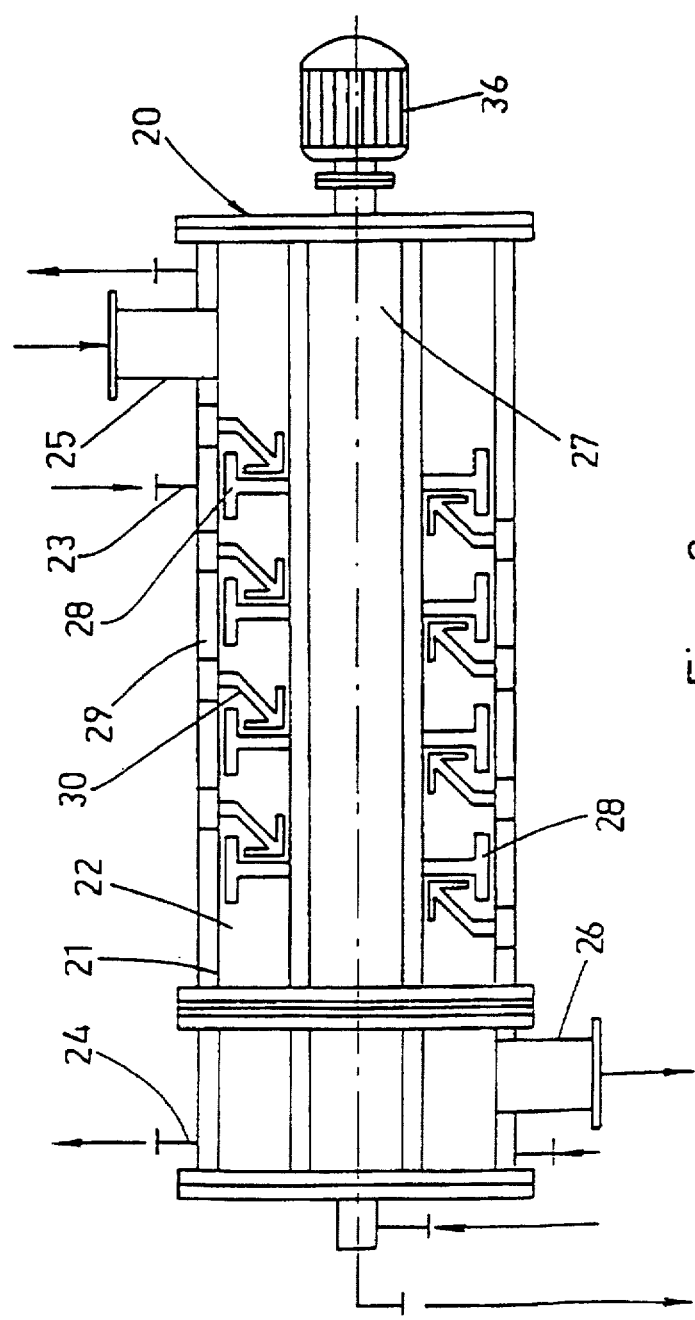
FIG. 3 is a transverse cross-section of the same machinery taken on plane III—III of FIG. 2.

The apparatus 20, illustrated in FIGS. 2 and 3, comprises an outer shell 21, which is tightly closed and insulates the inner space 22 from the ambient. Inert gas—generally nitrogen—is admitted through inlet 23 and discharged through outlet 24. However, any other means for maintaining in space 22 an atmosphere that is non-reactive to the treated product may be used according to the invention. The negative action of oxygen and light are thus prevented. The treated product is fed in molten form into said shell at 25 and is discharged therefrom in particulate form at 26. Substantially axially of the apparatus a shaft 27 actuated by motor 36 is provided, which carries rotary arms or agitators 28. Arms 28 provide a stirring and mixing action, which is required, although a single product and not a mixture is treated, to assure efficient heat transfer through the product mass and therefore a uniform temperature at each cross-section of the said mass, and apply a centrifugal force to the product, impelling particles of it upwards into the free space 22 above the product mass, to increase heat transfer and to produce, near the outlet 26, solid particles of the product. Cooling fluid is circulated through jacket 29 provided at the periphery of shell 21. The same fluid is also admitted into shaft 27 and flows from it to said rotary arms 28. Oil is preferred as a cooling fluid. Stationary arms 30 are provided in a position to interlock with and cooperate with the stirring arms and to remove therefrom any product that may have adhered thereto, which, with the passing time, would oxidize and produce black impurity specks. Thermometers for indication and control are provided at the stationary arms.

As an example of production plant an apparatus according to embodiment of FIGS. 2 and 3, used for the production of DHBP particles, has the following dimensions: outer shell diameter 420 mm; inner shell diameter 400 mm; shell length 1700 mm; diameter of the shaft 200 mm; number of rotary arms 45; number of stationary arms 30.

Important operational parameters for the method of the invention are the speed of rotation of the shaft and the ratio between the space occupied by the molten material being processed, and the total inner space of the apparatus. Typically, this latter ratio may vary from 50% to 75%, and may be, for example, about 70%. It is determined by the level of the product in space 22, which is determined, in turn, by a threshold or wear (not shown) provided at the outlet end of the apparatus, the upper level of which equals the upper level of the product, any product above said upper level being discharged from the apparatus. The product in the space 22 is impelled forwardly by the product entering the apparatus from inlet 25 and travels to the outlet end thereof while being stirred and mixed by rotary arms or agitators 28.

The rotary speed of the shaft varies greatly in various applications, and may be, for instance, between 5 and 50 turns per minute.

The heat exchange surface is partly provided by the housing and partly by the shaft and stirring arms, in approximately equal parts or with the surface of the housing being somewhat higher, e.g., 10 to 25% higher, than that of the shaft and stirrer arms. A moderate pressure over atmospheric pressure is usually maintained within the treatment space, to guarantee no infiltrations from the ambient, and may be, e.g., about 0.1 bar. A higher pressure will be maintained in the heating jackets and is a matter of design which need not be specified herein.

In order to produce finely subdivided particles, be they chips or flakes or granules, the rotation of speed of the shaft may be sufficiently higher to provide a desired centrifugal action. It will depend on the nature of the product, its viscosity in the molten state and the desired granulometry of the final product.

The product to be treated is fed into the apparatus, as has been said, in the molten state. The initial temperature will also be influenced by the viscosity that it is desired to obtain at the product inlet. Thereafter, the temperature curve along the apparatus will depend on the particular product treated. In the case of DHBP, the initial temperature is about 300° C. The cooling is continued until the product issues at a temperature of about 60° C. This temperature is much lower than that achievable by prior art solidifying and granulating systems.

When DHBP is treated, a product is obtained which is, to a very large extent, generally 94%, comprised between 2 mm and 0.1 mm. A smaller percentage, e.g., about 5%, has dimensions above 2 mm, and only a very small percentage, e.g., about 1%, has dimensions below 0.1 mm. There are almost no particles below 30μ present in the product.

The DHBP obtained is 99.5% pure, and has undergone practically no oxidation or degradation, as shown by an APHA value of 50 or less, which means the product has a very high degree of whiteness. X-ray analysis of the product shows that it is very highly crystalline.

Experience has taught that the granulometry of the final product can be controlled by acting on the speed of the shaft and the temperature of the cooling medium (water, oil). In the case of DHBP, the rotary speed of shaft 27, in a pilot plant apparatus, is from 5 to 50 rpm.

The volume space velocity (in the production plant), which is defined as the volume of product which passes through unit volume of the apparatus per hour, is from 0.5 $h^{-1}$ to 5 $h^{-1}$, preferably 0.8 $h^{-1}$ to 2.5 $h^{-1}$, for which the hourly production is from ~70 to ~210 kg/h.

EXAMPLE 1

The following example describes an experiment in pilot plant:

Product flow—20 kg/hr

Product's inlet temperature—290° C.

Product's outlet temperature—57° C.

Inlet cooling oil temperature—30° C.

Outlet cooling oil temperature—37° C.

Solidifier's r.p.m.—40 r.p.m.

Product's temperature along the solidifier—175° C., 120° C., 85° C., 57° C.

Particle size distribution:

| size mm | >2.0 | 2.0–1.4 | 1.4–0.6 | 0.6–0.21 | 0.21–0.1 | <0.1 |
|---|---|---|---|---|---|---|
| % weight | 2.8 | 2.6 | 35.5 | 54.7 | 4.1 | 0.3 |

Flowability properties: The product is free flowing, no adhesing properties and no arching.

Dimension's of the pilot plant solidifier:

inner shell diameter—170 mm.

shell length—930 mm.

While embodiments of the invention have been described by way of illustration, it will be apparent that the invention may be carried into practice by persons skilled in the art with many modifications, variations and adaptations, both as to the method variables and parameters and as to the structure of the apparatus used, particularly in view of the product treated in each case, within departing from the spirit of the invention or exceeding the scope of the claims.

We claim:

1. A method for the production of finely particulate solid chemical products from a molten stock, which comprises the steps of:

feeding the product, as molten stock, to an elongated treatment space, sealed from the ambient;

causing the product to flow as a flowable mass within space, while leaving a free portion of said space above the surface of said mass;

maintaining in said space an atmosphere that is non-reactive with said product;

subjecting said product to a stirring and mixing action by rotary means;

concurrently cooling said product as it proceeds along said space, whereby to solidify it;

concurrently detaching any product that adheres to surfaces within said space; and discharging the solidified product, in the form of solid particles, from said elongated treatment space.

2. Method according to claim 1, wherein the atmosphere that is non-reactive with the product is an inert atmosphere.

3. Method according to claim 1, wherein the molten product is cooled by heat exchange with cooled surfaces within as well as at the periphery of its fluid mass and in the free space above the surface thereof.

4. Method according to claim 1, wherein the elongated treatment space is substantially cylindrical.

5. Method according to claim 5, wherein the heat exchange within the fluid mass beings along a cylindrical surface about the axis of the cylindrical space and irradiates radially outwards therefrom.

6. Method according to claim 1, wherein the ratio of the fluid mass of the product treated and the volume of the treatment space is determined by the level of said mass within said space.

7. Method according to claim 6, wherein the level of said mass within said treatment space is determined by the level at which the solidified product is discharged from said space.

8. Method according to claim 1, wherein the ratio of the fluid mass of the product treated and the volume of the treatment space is comprised between 50% and 75%.

9. Method according to claim 8, wherein the ratio of the fluid mass of the product treated and the volume of the treatment space is comprised between 60% and 75%.

10. Method according to claim 1, wherein the forward flow of the product fluid mass along the elongated treatment space is produced by the feed of the molten product stock.

11. Method according to claim 1, wherein the volume space velocity of the product along the elongated treatment space is comprised between 0.5 $h^{-1}$ and 5.0 $h^{-1}$.

12. Method according to claim 1, wherein the chemical product treated is dihydro-biphenol.

13. Method according to claim 12, whereby the DHBP flowable particles are obtained with at least 99.5% purity, with at least 94% of said particles comprised between 0.1–2.0 mm, and with APHA value of at most 50.

14. Method according to claim 12, wherein the initial temperature of the product is about 300° C. and the product is cooled to about 60° C.

15. Use, for producing solid particles from a molten stock of a chemical product, of an apparatus comprising:

cylindrical shell defining an elongated inner space sealed from the ambient;

means for filling said space within said shell with non-reactive gas;

a plurality of rotary arms actuated for rotation by a shaft positioned substantially axially of said space;

a plurality of stationary arms positioned peripherally of said space for interaction with the rotary arms, to clean the same from adhered material, whereby to prevent its polimerization, decomposition or oxidation with the passage of time;

first cooling means, preferably located within said shaft and said rotary arms, for cooling any molten material located in said space;

second cooling means, located at the periphery of said shell inlet means for feeding a molten product stock to said space; and outlet means for discharging solidified product, in particulate form, therefrom.

16. Method according to claim 1, wherein the volume space velocity of the product along the elongated treatment space is comprised between 0.8 $h^{-1}$ and 2.5 $h^{-1}$.

* * * * *

UNITED STATES PATENT AND TRADEMARK OFFICE
CERTIFICATE OF CORRECTION

PATENT NO. : 5,698,142
DATED : DECEMBER 16, 1997
INVENTOR(S) : PRAGER ET AL.

It is certified that error appears in the above-identified patent and that said Letters Patent is hereby corrected as shown below:

Title page, [75] Inventors: "Nahara" should read —Naharia—

Title page, [56] References Cited, Other Publications: "Sumitomo" should read —Sumitimo—

Col. 1, line 59: "liens" should read —lines—

Col. 6, line 11: "claim 5" should read —claim 4—

Signed and Sealed this

Third Day of August, 1999

*Attest:*

Q. TODD DICKINSON

*Attesting Officer*     *Acting Commissioner of Patents and Trademarks*